United States Patent
Garito et al.

(10) Patent No.: US 7,137,982 B2
(45) Date of Patent: Nov. 21, 2006

(54) RF INTERVERTEBRAL ELECTROSURGICAL PROBE

(76) Inventors: Jon C. Garito, 3333 Royal Ave., Oceanside, NY (US) 11572; Alan G. Ellman, 3333 Royal Ave., Oceanside, NY (US) 11572

( * ) Notice: Subject to any disclaimer, the term of this patent is extended or adjusted under 35 U.S.C. 154(b) by 88 days.

(21) Appl. No.: 10/978,096

(22) Filed: Nov. 1, 2004

(65) Prior Publication Data
US 2006/0095034 A1    May 4, 2006

(51) Int. Cl.
*A61B 18/18* (2006.01)
*A61M 1/00* (2006.01)

(52) U.S. Cl. .............. 606/45; 604/35; 606/41; 606/48

(58) Field of Classification Search ........... 606/32–52; 604/35
See application file for complete search history.

(56) References Cited

U.S. PATENT DOCUMENTS

| | | | |
|---|---|---|---|
| 5,217,458 A | * | 6/1993 | Parins .................. 606/48 |
| 5,743,870 A | | 4/1998 | Edwards |
| 5,941,876 A | * | 8/1999 | Nardella et al. .......... 606/45 |
| 6,110,196 A | * | 8/2000 | Edwards ................. 607/96 |
| 6,296,638 B1 | * | 10/2001 | Davison et al. .......... 606/41 |
| 6,530,924 B1 | | 3/2003 | Ellman et al. |
| 2004/0034339 A1 | | 2/2004 | Stoller et al. |

FOREIGN PATENT DOCUMENTS

| | | |
|---|---|---|
| DE | 19641564 C1 | 5/1998 |
| EP | 0998879 A | 5/2000 |

* cited by examiner

*Primary Examiner*—Michael Peffley

(57) ABSTRACT

An electrosurgical instrument for spinal procedures comprises a generally scoop-shaped cup whose periphery is electrically active and is capable of applying RF electrosurgical currents to spinal tissue. The active electrode may comprise an exposed bare wire at the leading edge of the cup. A conduit in a handle section can convey suction to the cup. A tissue clearing member is pivotably mounted on or inside the cup and can be manipulated via a lever on the handle to help dislodge tissue. The tissue clearing member may be a radially-extending vane for rotation in the plane of the cup edge. The tissue clearing member may also be made electrically active thus selectively providing unipolar or bipolar operation.

13 Claims, 9 Drawing Sheets

RF INTERVERTEBRAL ELECTROSURGICAL PROBE

BACKGROUND OF THE INVENTION

Spine fusion is the current gold standard of care for low back pain today. Spinal devices and procedures currently available do not always completely eliminate the source of a patient's pain or restore the patient's natural disc function or range of motion. There is also some evidence that shows that fusion at a particular level may cause further degeneration to the discs at adjacent levels. Spinal Arthroplasty nowadays is becoming coming more popular as it potentially can significantly reduce pain, restore nearly full range-of-motion, and reestablish natural disc height thereby keeping the facet joints and surrounding ligament structure and tissue intact. Artificial disc prostheses and disc augmentation techniques have been under development for over 35 years. The evolutionary course of artificial disc product development has included an array of product designs, materials and instruments. Mechanical, elastometric and physiological solutions have been devices designed to replace the nucleus or a portion of the disc annulus.

Despite all the R&D, animal testing and human clinical trials so far spent on the problem, the preparation of the disc to accommodate the device is not well established. There is a need of a means to produce a precise void or cavity within the disc in a time-efficient manner while maintaining the viability of the vertebral endplates and integrity of the annulus fibrosis. If a procedure cannot properly manage anatomy preservation, it may not fully succeed.

Currently, mechanical devices such as rongures are being used without the ability to completely remove the nucleus material and the attempt often is time consuming. Many practitioners have dismissed lasers and electrosurgical devices on the ground that they produce excessive heat that can compromise the integrity of the endplates and annulus.

Various mechanical devices are described in the following patent publications: Nos. US2003/0040800A1 and US2004/0092943A1. These patents, the contents of which are herein incorporated by reference, also give details of the anatomy of the spine, nomenclature, and prosthetics.

SUMMARY OF THE INVENTION

An object of the invention is an improved surgical procedure for producing a void or cavity in human tissue.

Another object of the invention is an intervertebral electrosurgical electrode for forming a void in spinal tissue as part of a procedure for replacing spinal tissue with an artificial disc prosthesis.

We have invented a novel electrosurgical electrode for use in an electrosurgical intervertebral procedure. In accordance with one aspect of our invention, the novel electrode has an active end comprising a generally scoop shape whose periphery is electrically active and is capable of applying electrosurgical currents to human tissue with the result that a void or cavity or tunnel can be formed in the tissue to a considerable depth. The void or tunnel, at least initially, can have dimensions approximating the overall dimensions of the scoop-shaped electrode.

A further feature of the invention is the use of radio-frequency (RF) electrosurgical currents, in a frequency range preferably above 3 MHz, with 4 MHz being preferred.

It is believed that 4 MHz radiofrequency energy has been proven to be a self-limiting, minimal penetration energy source capable of precise tissue interaction. Thus, electrosurgical instruments that emit 3–4 MHz radiofrequency currents will be attractive to spinal surgeons needing to produce a space-specific nucleotomy efficiently and safely.

In combination with the innovative RF delivery system, i.e., the scoop-shaped electrode, radiofrequency energy can result in precision extraction of the nucleus pulposus and/or the entire disc that will enable a void to be created that will accommodate a replacement substance or device. The surgeon can exercise control of tissue vaporization as the focused energy emitted from the scoop-shaped electrode is rapidly and locally absorbed and liquefies the cells. Since lateral heat is typically not a byproduct of 3–4 MHz RF currents, damage to endplates can be minimized or avoided, nor will the RF currents violate the annulus.

Thus, an electrosurgical procedure using the novel electrode described herein enables physicians to offer to patients a treatment that is efficiently performed, relatively easily learned and thus performed at a significantly reduced price, and with less tissue damage and superior results compared to procedures done with other voiding devices. The electrode of the invention is uniquely configured to enable the active tip to reach and incise disc tissue while avoiding damage to surrounding disc tissues.

In a preferred embodiment, our novel electrode is characterized by an elongated electrically-insulated body portion having at a proximate end electrical contacts for receiving electrosurgical RF currents and preferably a fitting for receiving a suction conduit. The electrical contacts are internally connected to an active electrode at the distal end of the body portion, which active electrode comprises a generally annular conductive edge or exposed bare wire at the forward or leading edge of an open cylindrical or spherical member substantially in the form of a cup with or without a closing bottom. A conduit or duct in the body portion conveys the suction to the cup. In operation, while applying RF electrosurgical energy to the annulus periphery, the surgeon applies the active end to the tissue to be excised, typically by minimally invasive surgery (MIS), and manually manipulates the active end essentially to scoop out tissue which may become liquefied by the RF electrosurgical currents, while the removed tissue can be borne off by the suction for disposal. The tissue removal can be continued until the desired depth of the void left by the removed tissue is achieved. The action is effective both on the hard fibrosis annulus as well as on the soft inner pulpulus.

In a further preferred embodiment, a tissue clearing member is pivotably mounted on the scoop top edge, and is configured like an old-fashioned ice-cream scoop to sweep across the bottom surface of the scoop to dislodge and help remove any excess tissue not immediately suctioned away. The sweeping action can be controlled by the surgeon, preferably by mounting on the instrument handle a lever connected to the tissue clearing member and operable by the thumb of the surgeon to sweep the tissue clearing member around the inside of the scoop to dislodge any adherent tissue. In this preferred embodiment, the scoop shape is preferably semi-spherical.

In still a further preferred embodiment, the active end of the instrument is configured to provide two insulated electrodes, and connections are provided to the instrument such that only one of the electrodes can be made active for unipolar operation, or both of the electrodes can be made active for bipolar operation.

In yet a further preferred embodiment, a rotary member is rotatably mounted at the center of the cup so as to rotate in, or close to and parallel to, the plane of the active cup edge. The rotary member is electrically-conductive and can also be connected to the source of RF electrosurgical currents, and thus assists in resecting tissue along a well defined tunnel in the annulus.

The electrosurgical procedure has the very important advantage of being able to excise spinal tissue portions while at the same time coagulating the cut tissue causing minimum bleeding. It is preferred that the electrosurgical currents used be above 3 MHz, and preferably about 4 MHz. At these RF high frequencies, commonly referred to as radiosurgery, cutting is accomplished by volatilizing intracellular fluids at the point of the transmitting electrode contact which is primarily responsible for only small lateral heat spread and thus less damage to neighboring cell layers by keeping tissue temperature lower.

The advantages of using the intervertebral electrosurgical electrode of the invention include:

a) the RF low temperature energy source connected to the RF electrode enables precise micro cutting of the cutting edge into spinal tissue;

b) there is a reasonably clear unobstructed view of the surgical site with the intervertebral electrosurgical electrode of the invention.

When used herein with respect to the probe of the invention, the term "inward" means, with the electrode held by its handle, it is manipulated by the surgeon with respect to the tissue such that the active cutting edge acts as the leading edge moving into the tissue to be excised.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described preferred embodiments of the invention, like reference numerals or letters signifying the same or similar components.

DETAILED DESCRIPTION OF THE PREFERRED EMBODIMENTS

The novel design of the invention not only provides an active edge positioned for precise micro-cutting to remove well-defined segments of tissue exactly where the RF instrument is placed, but in addition the suction provided just inside the scoop simultaneously evacuates blood, tissue and RF plume from the surgical field for a clearer view.

Figure 1:
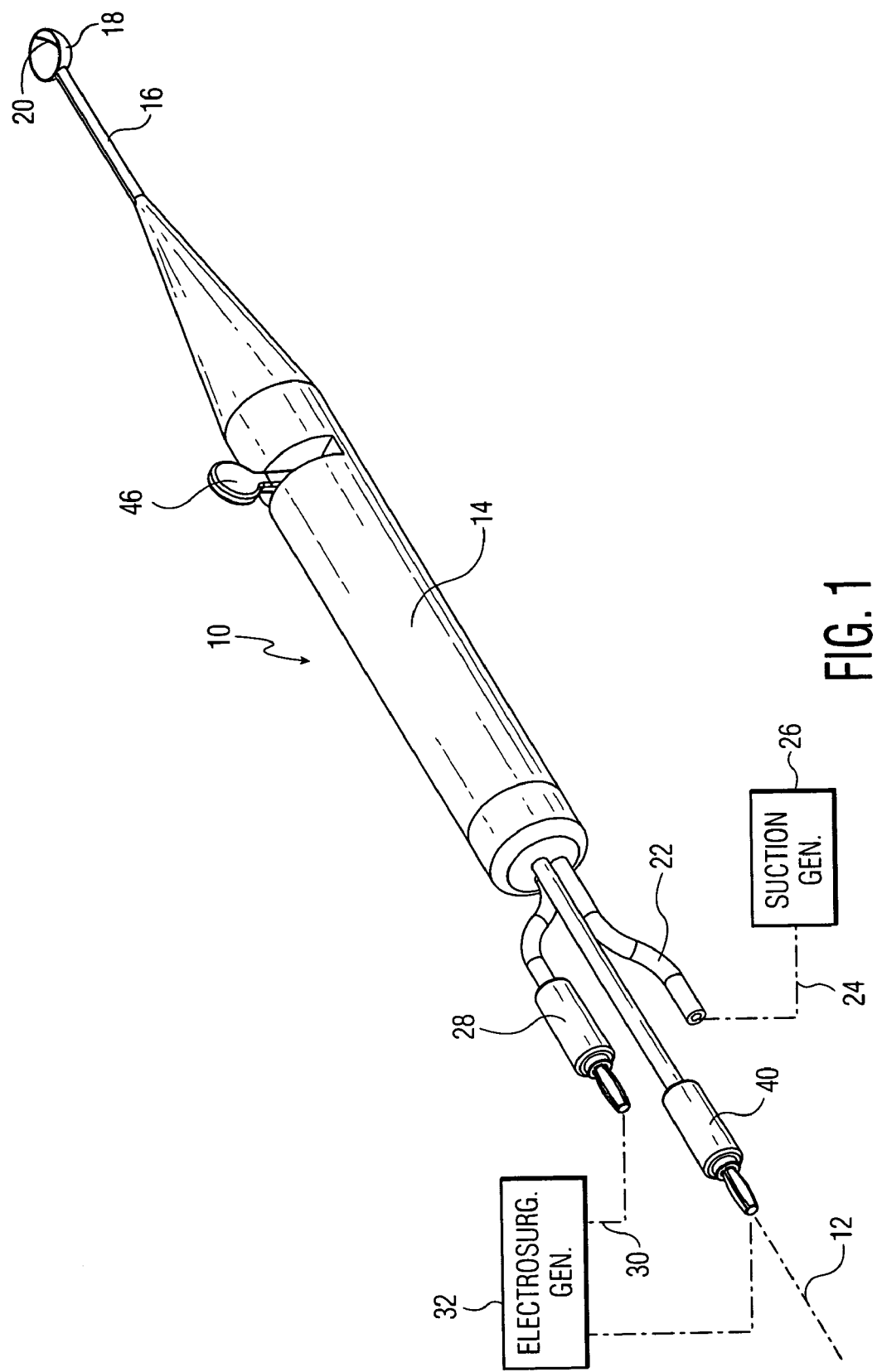
FIG. 1 is a perspective view of one form of intervertebral electrosurgical instrument of the invention shown schematically connected to electrosurgical apparatus and a suction generator.
Figure 2:
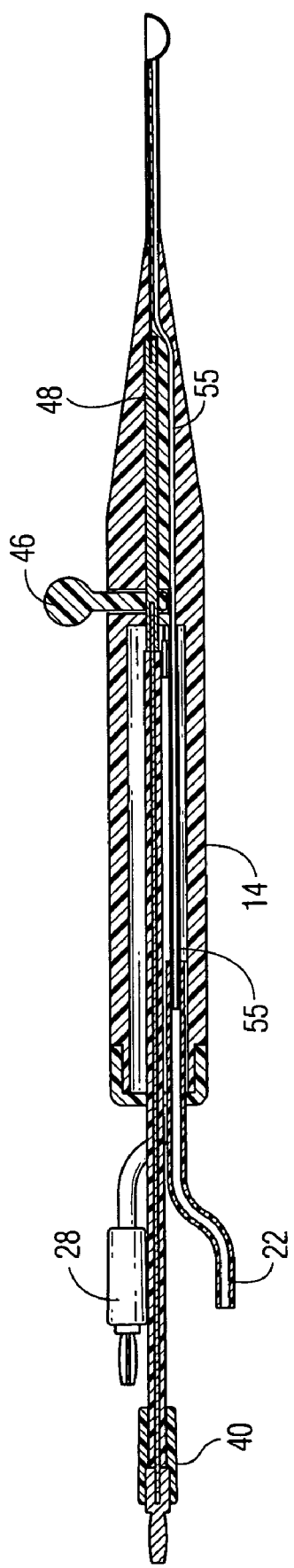
FIG. 2 is a partly cross-sectional view of the intervertebral electrosurgical instrument of FIG. 1.
Figure 3:
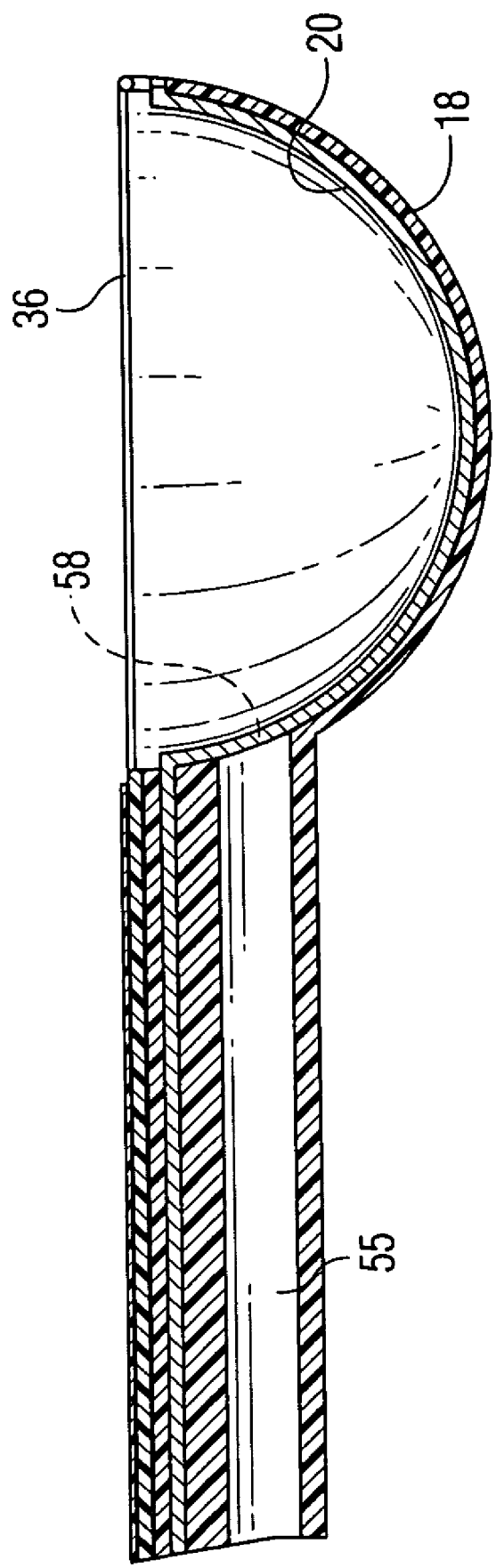
FIG. 3 is an enlarged cross-sectional view of the active working end of the intervertebral electrosurgical instrument of FIG. 1.
Figure 4:
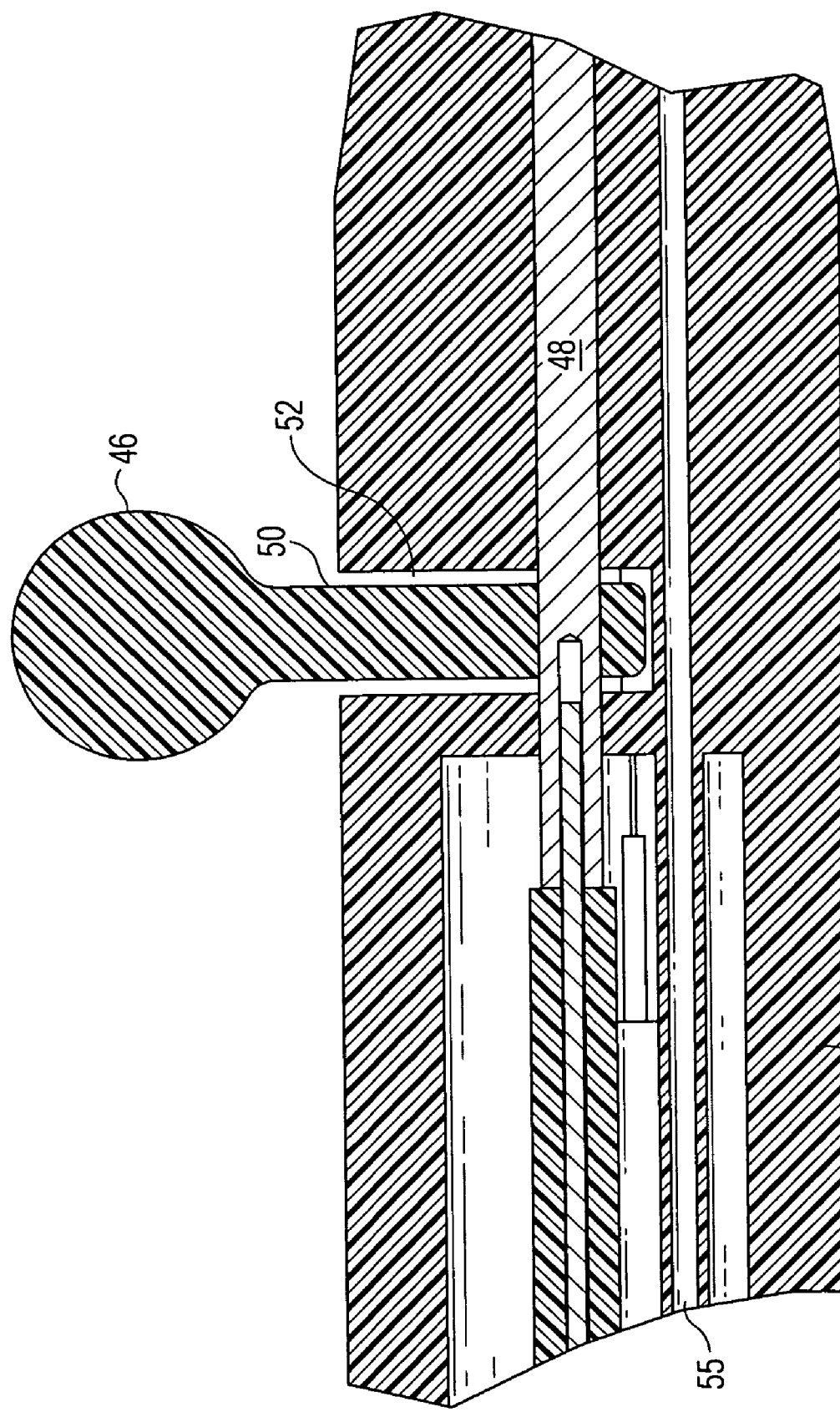
FIG. 4 is a an enlarged cross-sectional view of the lever system that operates the active working end of the intervertebral electrosurgical instrument of FIG. 1.

FIG. 1 illustrates a preferred form of the novel intervertebral electrosurgical instrument 10 of the invention. It comprises an elongated structure having a central axis 12 including at a proximate first end (at the left of FIG. 1) a handle 14 and at the opposite distal second end a shaft 16 terminating in a upwardly extending semi-spherical scoop 18 on the bottom of which is mounted a tissue clearing member 20 (only visible as a line in FIG. 1). At the first end is mounted a fitting 22 for receiving a conduit (shown schematically) 24 capable of supporting suction. The conduit in turn is connected to a conventional suction generator 26. At the same first end is mounted a first male electrical connector 28 which is connected via a cable 30 in the conventional manner directly or via an adaptor to the unipolar socket of conventional electrosurgical apparatus 32. As an example only, and not meant to be limiting, the electrosurgical apparatus 32 can be model AAOP Surgitron FFPF or the Dual-Frequency Unit available from the Ellman company of Oceanside, N.Y. The Ellman equipment is preferred due to its high operating frequency, typically over 2 MHz, preferably at 3.8–4 MHz.

The handle 14 and shaft 16 including the scoop 18 as a unitary body are constructed of electrically-insulating material, such as of a suitable plastic such as ABS. The electrical connector 28 is electrically connected via a wire 34 to an electrically-conductive wire loop 36 that is mounted on top of the open scoop edge. The result is that the wire loop 36, for example, of stainless steel, mounted on the scoop edge, is electrically connected via the electrical connector 28 to a unipolar socket on the electrosurgical apparatus 32. Hence, when the electrosurgical unit 32 is activated, electrosurgical currents flow via the connector 28 to the loop 36 at the scoop top.

A second connector 40 is connected via a wire 42 to the tissue clearing member 20 which in this example is a semi-circular wire that has the same configuration as the semi-spherical scoop 18 and thus can sweep along the scoop bottom when rotated in the same manner as the old-fashioned ice-cream scoop that functions to remove scoops of ice cream from inside the scoop. The second connector 40 may be, optionally, plugged into one socket of a bipolar socket on the electrosurgical apparatus. The wire loop 36 and sweep-clearing wire 20 are configured such that the two electrically-conductive wires are electrically-insulated from one another at all times.

This construction thus provides, selectively, unipolar operation when only the connector 28 is connected to the electrosurgical apparatus and the usual indifferent plate is connected to the patient's body, and if desired bipolar operation by connecting both connectors 28, 40 to a bipolar socket of the apparatus. In the case of unipolar operation, only the wire loop 36 is active and electrosurgical currents flow from it to the patient's tissue and then return via the indifferent plate. In the case of bipolar operation, the electrosurgical currents flow and are confined between the active wire loop 36 and the active tissue clearing member 20. Activation of the electrosurgical apparatus 32 can be accomplished by means of the usual foot switch (not shown), or, as is well known in the art, fingerswitches can be added to the housing 14 to selectively connect the connectors 28, 40 to their respective active wire during the surgical procedure.

Figure 5:
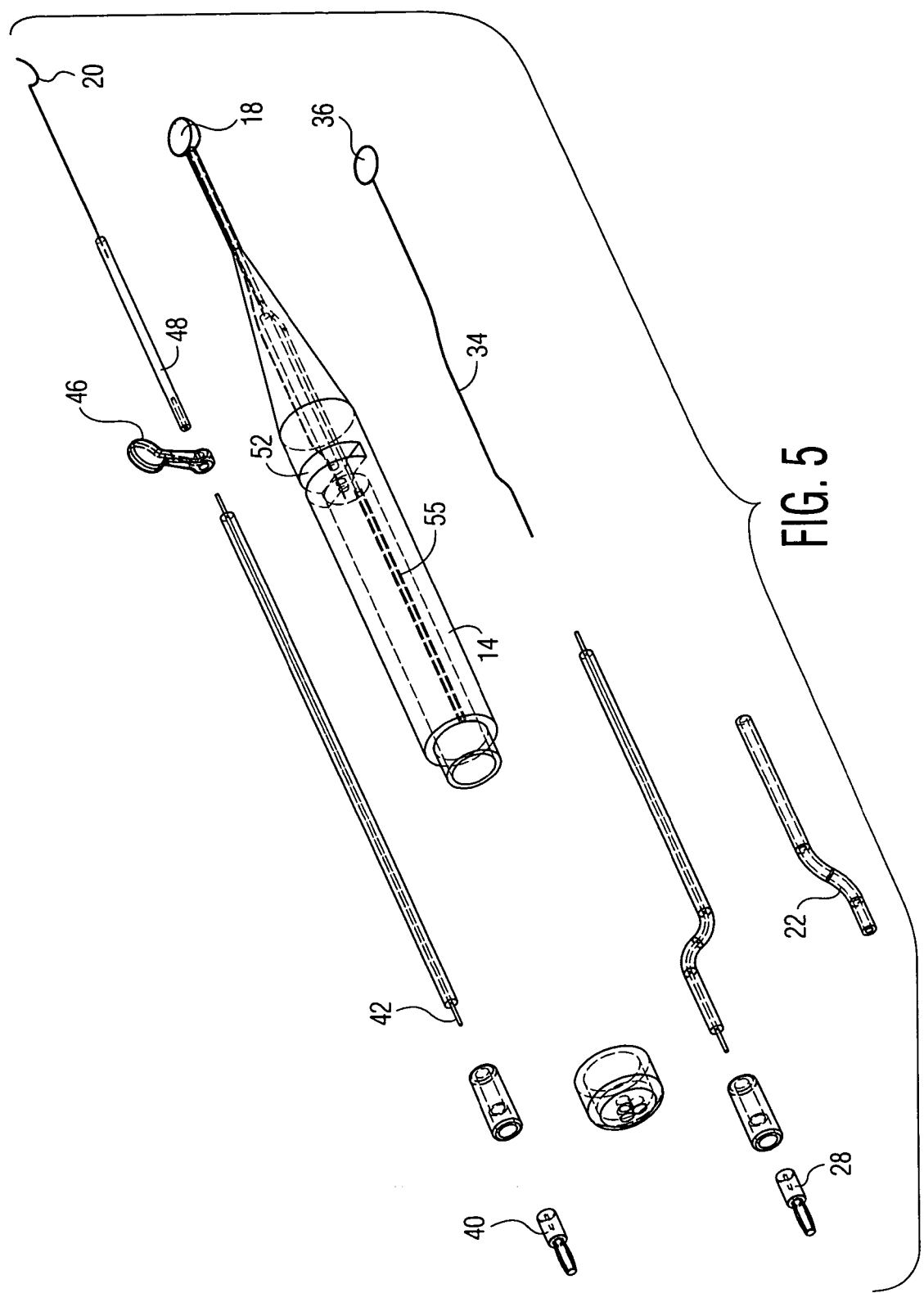
FIG. 5 is an exploded view of the instrument of FIG. 1.
Figure 6:
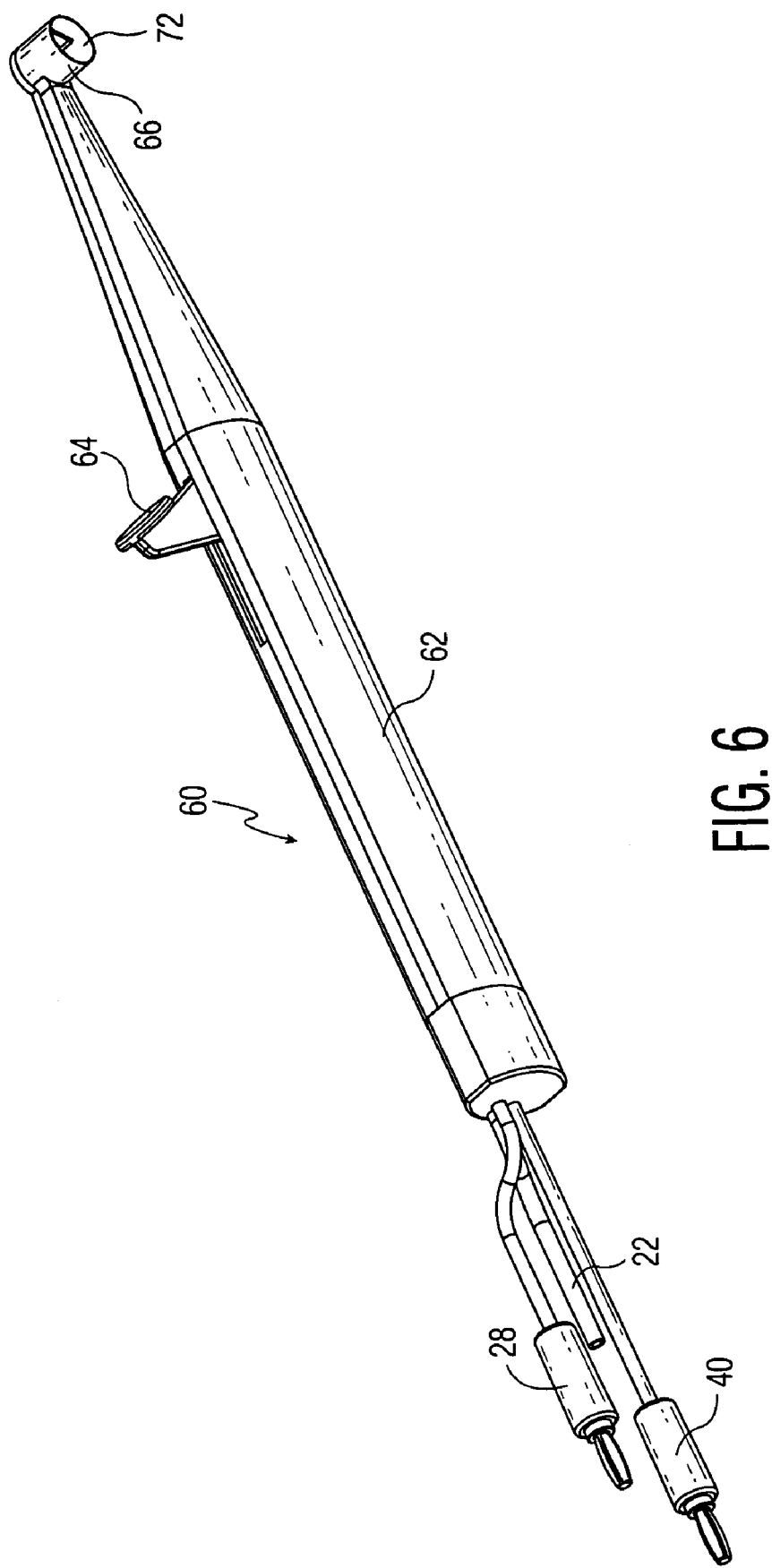
FIG. 6 is a perspective view of another form of intervertebral electrosurgical instrument of the invention.
Figure 8:
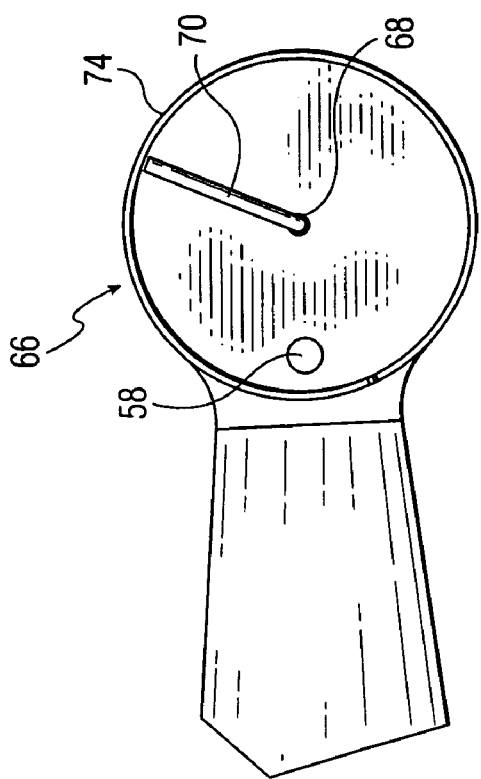
FIG. 8 is an enlarged bottom view of the active working end of the intervertebral electrosurgical instrument of FIG. 6.
Figure 7:
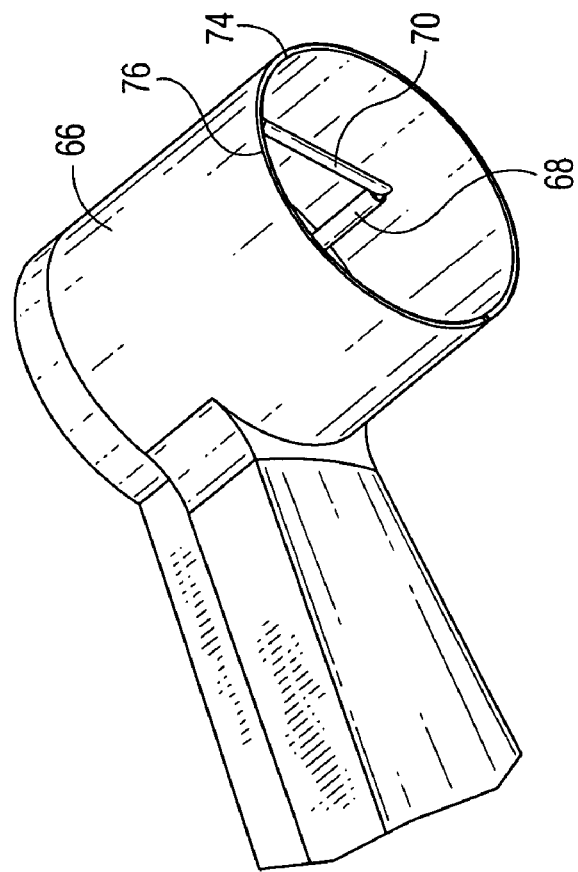
FIG. 7 is an enlarged perspective view of the active working end of the intervertebral electrosurgical instrument of FIG. 6.

Activation of the tissue clearing member 20 is preferably accomplished by means of a thumb-activated pivotably-mounted electrically-insulated lever 46 connected fixedly to a metal shaft 48 to which the tissue clearing member 20 is connected (see FIG. 5). The lever arm 50 is mounted in a semi-circular slot 52 and thus is free to rotate over an angle of about 90°, which is not critical. The degree of rotation should be sufficient to allow the semi-circular wire 20 to sweep from one edge to the opposite edge of the scoop, i.e., across substantially the entire inside of the scoop.

The suction duct 22 is pneumatically connected via an internal canal 55 in the body from the duct end 22 to an opening 58 in the scoop rear by which the suction when activated will clear the scoop of any vapors or liquids or small tissue bits left behind when the scoop end scoops out tissue during a procedure.

It will be apparent from the foregoing description that the intervertebral electrosurgical instrument 10 of the invention can be constructed with just the unipolar feature or with just the bipolar feature or with both as illustrated.

FIGS. 6–10 illustrate another embodiment 60 of the invention wherein the tissue-clearing member is a rotary vane. In this embodiment, it is preferred that the cup have a cylindrical shape. In the perspective view of FIG. 6, the non-working end at the left of the drawing is similar to that in the FIG. 1 embodiment, with a suction tube 22, and two electrical connectors 28, 40 extending out of the back of the tubular housing 62 that serves as the instrument handle. There is also a thumb-activating lever 64 present in this embodiment that is operably connected to the working end at the right of the drawing. The working end in this instance comprises a cylindrical scoop- or cup-shaped member 66 along the center axis of which is mounted an axle 68 connected to a radially-extending vane or element 70. The mounting is such that the radial element can rotate in a plane parallel to the open face 72 of the cup together with its axle 68, when the latter is rotated. As before, one electrode comprises a loop 74 mounted at the cup leading edge 76. Preferably, the free end of the radial element 70 rides within a narrow annular recess (not shown) inside the cup cylinder to stabilize its action and maintain it in its position while rotating parallel to or in the plane of the cup face 72.

Figure 9:
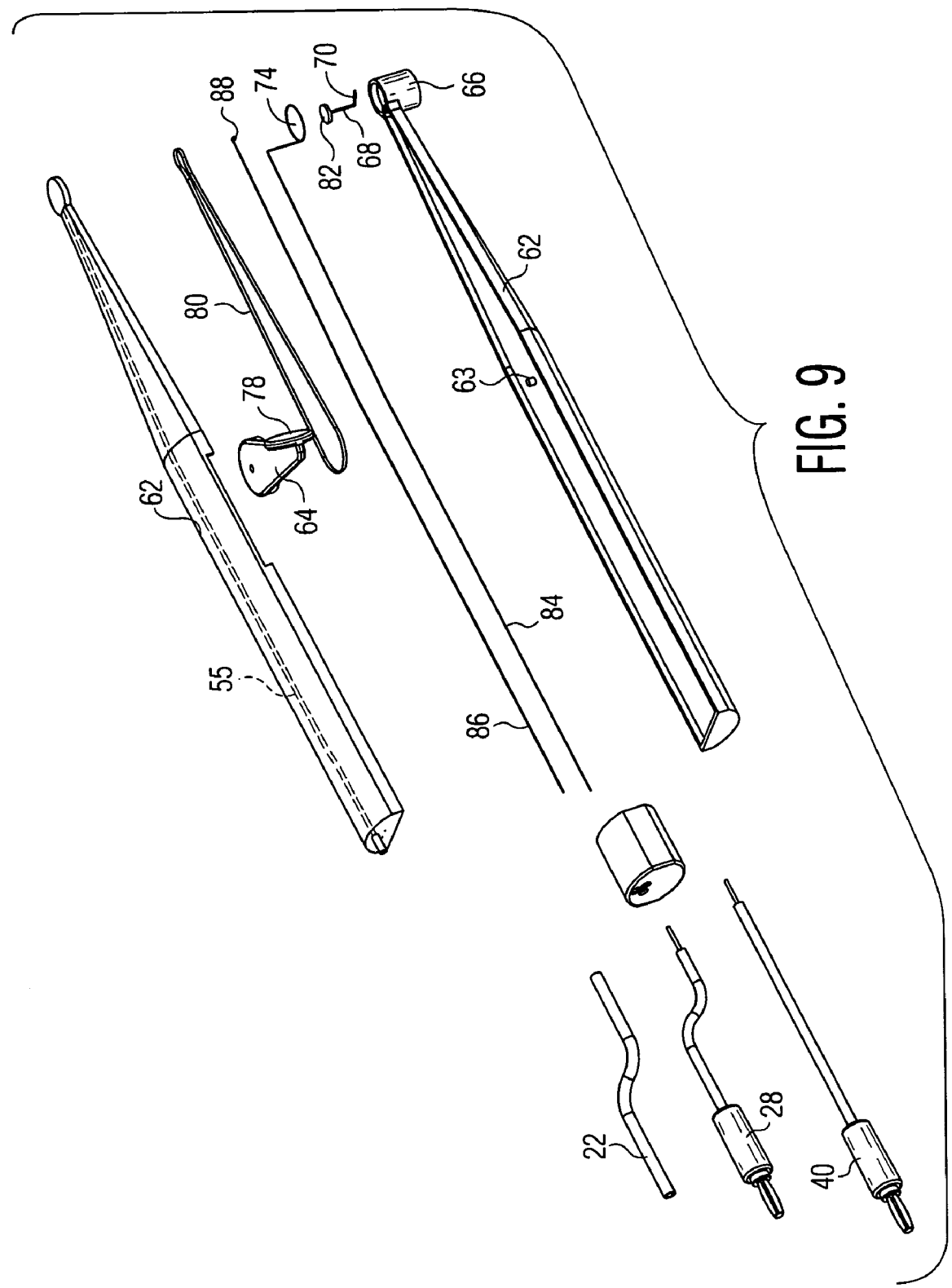
FIG. 9 is an exploded view of the instrument of FIG. 6.
Figure 10:
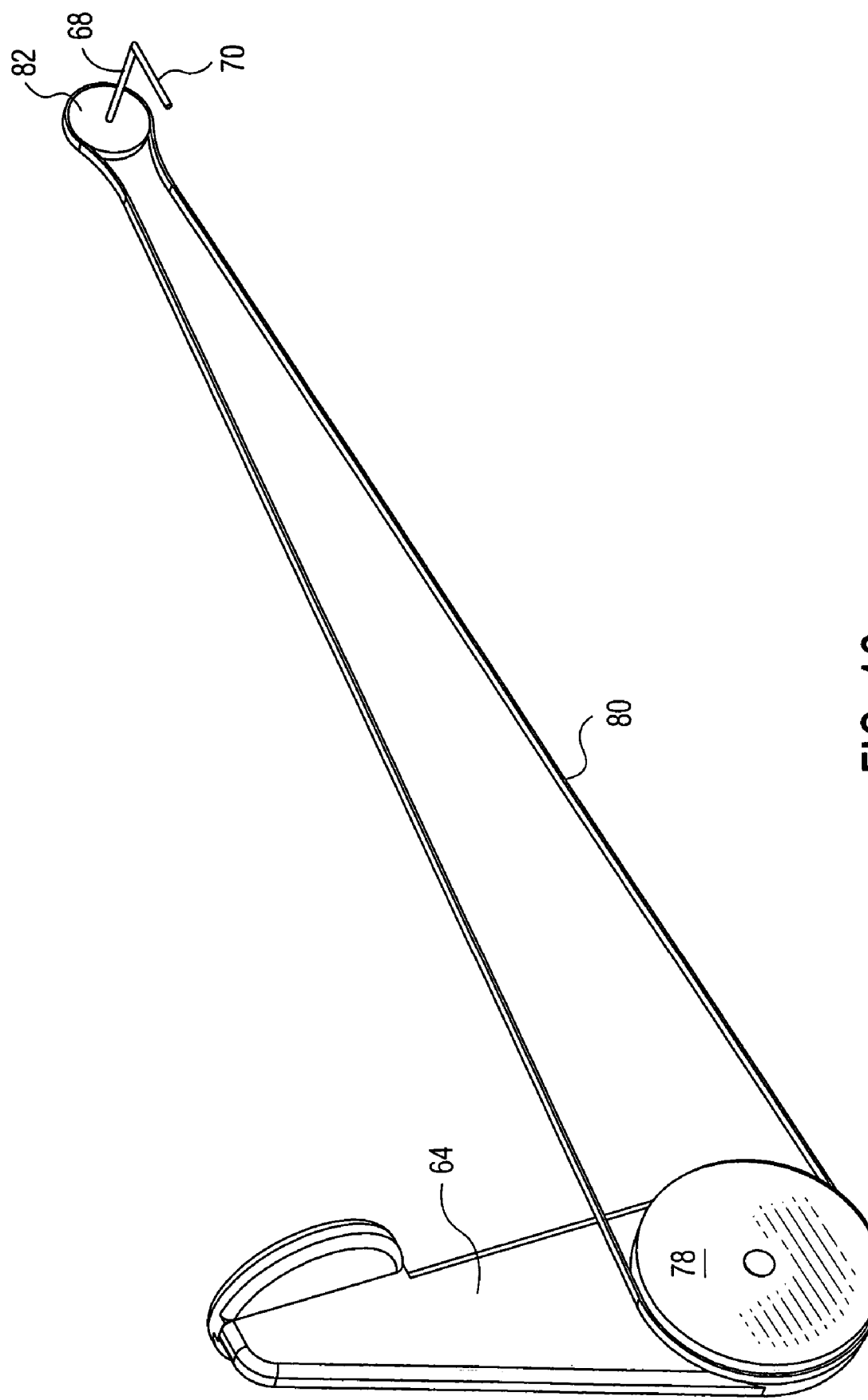
FIG. 10 is a perspective assembly view of the moving parts of instrument of FIG. 6.

FIGS. 9 and 10 illustrate one way of causing the rotary element or vane to rotate when the thumb-activated lever is operated by the surgeon. Connected to the end of the lever 64 inside the housing is a cylindrical surface 78, in the plane of the lever, that acts as a first driving pulley for a closed loop belt 80. The opposite end of the belt 80 is connected to a second smaller disk 82 serving as a second driven pulley and on which is mounted, perpendicularly to the disk surface, the axle 68 for the rotatable vane 70 that functions as the tissue-clearing member. Due to the geometry, with the lever 64 extending essentially at right angles to the cup axis, when the lever is pushed down by the user's thumb from its position shown in FIG. 6, rotating about a small projection 63, the first pulley disk 78 rotates the belt 80 which in turn rotates the second pulley disk 82 and thus the tissue-clearing vane 70 connected to it. The different pulley sizes are such that the thumb motion is amplified so as to cause one complete revolution of the tissue-clearing vane 70 before the lever reaches the end of its downward motion.

The radially-extending vane 70 is of bare metal and electrically active, as is the wire loop 74 partially embedded in the cup leading edge 76 so that at least a top bare part is exposed and active. A first electrical connection to the loop 74 is made via the connector 28 and longitudinally-extending conductor 84 (FIG. 9). A second electrical connection to the tissue-clearing vane is made via the connector 40 and longitudinally-extending conductor 86. At the tip of the latter is a short perpendicularly projecting electrically-conductive end 88 that is configured to remain always in electrical contact with the top surface of the metal disk 82 when the parts are assembled and while the tissue-clearing vane 70 is rotated. That continuous electrical contact maintains the tissue-clearing vane 70 electrically active whenever the second connector 40 is plugged into the electrosurgical apparatus 32 and activated.

In operation, the surgeon manipulates the handle 60 with the leading edge loop 74 active for unipolar operation while pressing the leading edge into the spinal tissue and forcing the tissue into the cup 66, the tissue in the cup being removed via the suction connection 22 and interior channel 55, whose opening into the cup is shown at 58. Whenever deemed necessary, the surgeon can operate the tissue removing lever 64 to cut off the tissue inside the cup from that outside the cup allowing the suction room to perform its extraction function. Alternatively, the surgeon can electrically activate the tissue-clearing vane 70 during this excising action or while the cup is being pressed into the tissue to obtain bipolar operation. As with the first embodiment, the instrument can be constructed with just the loop 74, or with just the vane 70, or with both as illustrated for the most versatility in operation. To ensure that the two electrodes remain electrically-insulated, it is preferred that the tissue-clearing vane 70 in its rotating path is positioned just below the exposed surface of the loop 74 at the cup leading edge 76.

It will be appreciated that other ways of providing a constant electrical connection between moving parts can be substituted for that illustrated as will be evident to those skilled in this art.

The whole instrument 10, 60 in use is typically made from electrically-insulating material or covered by a plastic coating, except for the two active electrodes 20, 36 or 70, 74. Hence, during use, the entire assembly apart from the electrodes is shielded from the electrosurgical currents and thus prevented from inadvertently causing injury to the patient.

In order for the instrument of the invention to perform an intervertebral procedure, certain dimensions of the scoop are important for the active end to reach the desired spinal tissue and/or create a channel to reach interior tissue to be excised. In the preferred embodiments, the wire loops 36, 74 preferably have a wire diameter of about 0.005–0.03 inches. The width across the scoop top, i.e., the scoop diameter, for both the semi-spherically- 18 and cylindrically-shaped 66 scoops, preferably is about 0.5–2.0 inches. For the cylindrical scoop embodiment, the depth of the cup-shaped member is about 0.1–2 inches. The tissue-clearing wire 20 may be of the same stainless steel wire as the wire loop but sufficiently stiff to perform its tissue-clearing function. The suction channel 55 should have sufficient size to allow a reasonable negative pressure to exist at the surgical site.

The entire structure which constitutes a unipolar or bipolar probe is stiff and sturdy and does not flex during use. The scoop dimensions may be reduced for use of the probe with very small children. Also connected to the electrosurgical unit 32 is the usual indifferent plate which during use is in contact with the patient's body. When the electrosurgical apparatus 32 and suction generator 26 are energized, high frequency electrosurgical currents are generated which are coupled by way of the electrically conductive wires in the handle body 14 (FIG. 1) to the active wire loop end 36 and tissue clearing member 20 if bipolar operation is employed. The physician, in the usual way, holds the handle 14 while applying the working scoop end 18 of the probe to the desired area of the patient to be treated. Any smoke or blood is evacuated under the suction produced at the suction end 58 which is closely spaced to and thus effective at the scoop interior and thus at the surgical site. The electrosurgical currents simultaneously with the excising will coagulate any bleeders avoiding excessive blood and other fluids that may obstruct vision of the surgeon.

From the description and drawings it will be clear that the electrically insulating nature of the assembly including the scoop body except for the active bare wires 36, 20 functions to prevent undesired contact and possible burns by those members to adjoining and surrounding tissue.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. An electrosurgical instrument for excising of tissue, comprising:
   (a) an elongated handle portion having a longitudinal axis and comprising at a proximate end electrical contacts for receiving electrosurgical RF currents and a fitting for receiving suction,
   (b) a suction conduit within the handle portion and connected at one end to the fitting,
   (c) the handle portion having at a distal end a generally cup-shaped fixed member having an open top with an annular leading edge and an interior, the cup-shaped member having a closed rear portion, with the rear portion being electrically-insulating with respect to externally-contacted tissue.
   (d) an active electrode at the distal end of the handle portion, the active electrode comprising a bare annular electrically-conductive element provided at the annular leading edge of the cup-shaped member,
   (e) means for connecting the electrical contacts to the active electrode,
   (f) the suction conduit at its distal end opening from the rear portion and facing into the interior of the cup-shaped member providing access for the suction to the cup interior,
   (g) portions of said handle portion except for the active electrode being electrically insulating to prevent contact and passage of electrosurgical currents to areas adjacent to or surrounding the tissue to be excised when electrosurgical currents are supplied to the electrical contacts and suction applied to the fitting during a surgical procedure.

2. An electrosurgical instrument for excising of spinal tissue by a surgeon, comprising:
   (a) an elongated handle portion having a longitudinal axis and comprising at a proximate end at least a first electrical contact for receiving electrosurgical RF currents and a fitting for receiving suction,
   (b) a suction conduit within the handle portion and connected at one end to the fitting,
   (c) the handle portion having at a distal end a generally open cup-shaped member having an annular leading edge,
   (d) an active electrode at the distal end of the body portion, the active electrode comprising a bare annular electrically-conductive element provided at the annular leading edge of the cup-shaped member,
   (e) first means for connecting at least the first electrical contact to the active electrode,
   (f) the suction conduit having at the distal end an opening facing into the interior of the cup-shaped member,
   (g) portions of said handle portion except for the active electrode being electrically insulating to prevent contact and passage of electrosurgical currents to areas adjacent to or surrounding the tissue to be excised when electrosurgical currents are supplied to the electrical contacts and suction applied to the fitting during a surgical procedure,
   (h) a tissue-clearing member mounted for movement within the cup-shaped member,
   (i) an activator mounted on the handle and operatively connected to the tissue-clearing member and operable by a user to move the tissue-clearing member to dislodge tissue in the cup-shaped member.

3. An electrosurgical instrument as claimed in claim 2, further comprising at the proximate end of the handle at least a second electrical contact for receiving electrosurgical RF currents, and second means for connecting the second electrical contact to the tissue-clearing member, whereby either the active electrode at the leading edge or the tissue-clearing member can be selectively activated for unipolar operation or both the active electrode and the tissue-clearing member can be selectively activated for bipolar operation.

4. An electrosurgical instrument as claimed in claim 2, wherein the cup-shaped member is semi-spherical having an inside surface, and the tissue-clearing member comprises a curved vane mounted and configured to sweep along the inside surface of the cup-shaped member to dislodge any tissue present therein.

5. An electrosurgical instrument as claimed in claim 2, wherein the cup-shaped member is cylindrically-shaped, and the tissue-clearing member comprises a radially-extending vane axially-mounted within the cup-shaped member and configured to sweep in a path parallel to the plane of the leading edge of the cup-shaped member to dislodge any tissue present therein.

6. An electrosurgical instrument as claimed in claim 2, wherein the first means comprises a wire extending inside the handle from the first contact to the active electrode at the leading edge.

7. An electrosurgical instrument as claimed in claim 3, wherein the first means comprises a first wire extending inside the handle from the first contact to the active electrode at the leading edge, and the second means comprises a second wire extending inside the handle from the second contact to the tissue-clearing member.

8. An electrosurgical instrument as claimed in claim 7, wherein the second means comprises a disk connected to the tissue-clearing member and a wire contacting the surface of the disk and configured to maintain that contact when the tissue-clearing member rotates.

9. An electrosurgical instrument as claimed in claim 2, wherein the active electrode comprises a wire with a wire diameter of about 0.005–0.03 inches.

10. An electrosurgical instrument as claimed in claim 2, wherein the cup shaped member has a width across its top of about 0.5–2.0 inches.

11. An electrosurgical instrument as claimed in claim 2, wherein the cup shaped member has a depth of about 0.1–2 inches.

12. The electrosurgical instrument of claim 2, in combination with:
   (a) an electrosurgical apparatus capable of supplying high frequency electrosurgical currents to the first electrical contact,
   (b) a suction generator for receiving the suction fining.

13. The combination of claim 12, wherein the high frequency currents are at a frequency of about 4 MHz.

* * * * *